United States Patent [19]

Ludvigsen

[11] Patent Number: 5,231,032
[45] Date of Patent: Jul. 27, 1993

[54] METHOD OF MONITORING BLOOD LOSS

[75] Inventor: Bernard Ludvigsen, Mobile, Ala.

[73] Assignee: University of South Alabama, Mobile, Ala.

[21] Appl. No.: 681,896

[22] Filed: Apr. 8, 1991

[51] Int. Cl.$^5$ ............................................. G01N 33/72
[52] U.S. Cl. .................................. 436/66; 436/177; 422/20; 435/2; 128/648; 210/748
[58] Field of Search .................... 436/66, 165, 177; 128/637, 638; 422/20; 435/2; 210/646, 748

[56] References Cited

U.S. PATENT DOCUMENTS

| | | | |
|---|---|---|---|
| 3,492,095 | 1/1970 | Tillem | 436/66 |
| 4,193,818 | 3/1980 | Young et al. | 422/20 X |
| 4,428,800 | 1/1984 | Tarcy | 436/124 X |
| 4,562,842 | 1/1986 | Morfeld et al. | 128/638 |
| 4,766,080 | 8/1988 | Fleming | 436/164 X |
| 4,773,423 | 9/1988 | Hakky | 128/637 |
| 4,853,338 | 8/1989 | Benezra et al. | 436/66 |

Primary Examiner—James C. Housel
Assistant Examiner—Maureen M. Wallenhorst
Attorney, Agent, or Firm—Oblon, Spivak, McClelland, Maier & Neustadt

[57] ABSTRACT

Blood loss by a patient during an operation is monitored by collecting all blood and bloodied materials generated during the operation and subjecting them to ultrasonic vibration in a buffered eluent containing a volume control substance by which the actual volume of the blood-added eluent can be determined. Hemoglobin concentration in the eluate is measured periodically or continually, and multiplied by the eluate volume, to give the actual hemoglobin lost. This value is adjusted by the hemoglobin concentration of the patient just prior to the operation, to give the actual blood volume lost. The blood lost during the operation can also be monitored continuously, and real time values provided.

11 Claims, 2 Drawing Sheets

METHOD OF MONITORING BLOOD LOSS

FIELD OF THE INVENTION

The invention addressed herein is a method for determining blood loss in a mammalian patient undergoing an operation with the potential for blood loss. Specifically, a method of measuring blood loss, giving real time, or real time plus a few minute values, to determine the need for, and amounts of, suitable transfusions, is provided.

BACKGROUND OF THE INVENTION:

The importance of determination of the amount of blood lost by a patient undergoing a surgical operation, human or animal, is well documented. Thus, the need for simultaneous and subsequent transfusions, anesthesiology and recovery measures, subsequent therapeutic treatments, and post-operative diagnosis and prognosis, are all dependent, to at least some degree on obtaining an idea of the amount of blood lost by a patient during an operation. The greater the amount of blood lost or potential amounts of blood to be lost, the greater the need for accurate determination of actual blood lost during the procedure. Simultaneously, however, the greater the actual amount of blood lost by the patient, the less accurate estimates by those in the operating theater, including the surgeon and anesthesiologist, become. Thus, determinations of the need for transfusions and the like become increasingly difficult as operations involving high degrees of blood loss are encountered.

Another difficulty stems from the fact that the patient's current hemoglobin concentration does not accurately reflect the patient's remaining oxygen-carrying capacity. Administration of intravenous fluids may tend to diminish the hemoglobin values, and blood loss alone will not affect the concentration significantly until many hours later.

Simultaneously, the nation's blood supply has been severely threatened. Thus, the increase in AIDS, as well as traditional contaminating factors, such as HBV, have limited the available blood supply, and also pose increasing hazards to those receiving a transfusion. This highlights the need to have an accurate determination of the amount of blood lost, to determine the need for a transfusion, and if such a need is determined, exactly the quantity of transfusion to be contemplated.

U.S. Pat. No. 4,773,423 describes a method for determining blood loss. In the described process, blood is collected via a vacuum tubing, and blood is urged from collected swabs and the like, and thereafter the amount of blood lost is determined on the basis of hemoglobin content. The process presents two problems. Initially, it is noted that it is difficult, by direct vacuum suctioning, to obtain all of the blood lost by the patient. Particularly during lengthy preparations, large amounts of blood may be deposited on instruments, lost in absorbent pads, sponges and the like, which are difficult to remove on mere urging. U.S. Pat. No. 4,773,423 does not describe the method for obtaining close to 100% of the blood lost in this method. Moreover, the method described in U.S. Pat. No. 4,773,423 relies on direct color measurement of the reagent solution. Such direct measurement is difficult, particularly in light of the fact that hemoglobin is generally a mixture of varying forms, each with its own absorption spectrum, and any fluid obtained from a patient will also be complicated by a variety of dissolved and solid impurities, and debris, presenting a high degree of turbidity, and complicating direct colorimetric measurement. Alternate forms, based on measuring iron content and the like, may not give a true reading, because of the likelihood of the presence of iron in the patient's tissues, and materials employed i the operating theater.

To a similar end, a blood-loss monitor is described in the Lancet, Oct. 8, 1977, which calls for the washing of swabs and drapes on which blood is collected, followed by photocolorimetry. Again, no method is provided for directly reading hemoglobin content. Experience has demonstrated that such direct colorimetry gives unreliable values.

Accordingly, it remains a goal of those of ordinary skill in the art to provide a method for determining blood loss of a patient undergoing a surgical operation, on a real time or real time plus no more than five-minute basis, that is not dependent on direct colorimetry, or other uncertain measurements.

SUMMARY OF THE INVENTION

All bloodied materials, bearing blood generated during the operation, are collected in a tank with an eluting fluid, the eluent being a weak buffer, having a pH of 5.8–6.8. The buffer, of low ionic strength, has a known initial volume. Prior to initiation of the operation, the eluent is provided with a known concentration of an ion not likely to be obtained from either the patient, or materials used in conjunction with the operation, to provide a volume control. Lithium is one example of an ionic analyte. The analyte must be one whose concentration can be determined o the basis of use of an ion-selective electrode.

To this eluent, all blood-bearing materials are added, either liquid or solid, in an enclosure capable of providing ultrasonic vibration to the eluent. In this manner, effectively 100% of the blood borne by the solid materials and all liquid blood-bearing materials, are liberated, to produce a buffer-based blood-containing eluate.

Samples of the eluate are taken at periodic intervals, for analysis of hemoglobin content. Hemoglobin content is measured by a 2-step spectrohotometric determination. The eluate sample is treated with potassium ferricyanide, converting all Hb to methemoglobin. The sample is photometrically assayed at either 632 nm or 540 nm, the absorbance values for methemoglobin and cyanomethemoglobin, respectively. Cyanide is added to convert the Hb present to cyanomethemoglobin. The sample is read again, at the selected frequency. The difference (an increase if 540 nm is used, a decrease at 623 nm) in the values is proportional to the Hb present in the sample.

The actual eluate volume is determined by measuring the concentration of the ion added to the eluent prior to the operation, e.g., $Li^+$. The resulting proportion gives the current volume of eluate. By simple multiplication of the Hb concentration, times the eluate volume, the amount of Hb (expressed in mass units) lost can be determined.

By having measured the Hb concentration of the patient's blood immediately prior to the operation, the amount of blood lost, expressed in volume units, can be obtained from the mass of Hb determined above. Thus, a determination of the need for, and amount of blood to be supplied by transfusion, can be directly obtained.

By computer automation, real time values, or real time plus a few minutes, no more than five minutes, can be provided to the operating theater, thus providing information on the amount of blood lost, useful in determining the acceptable length of an operation, the patient's status, and the need to provide a transfusion simultaneous with the operation.

Figure 1:
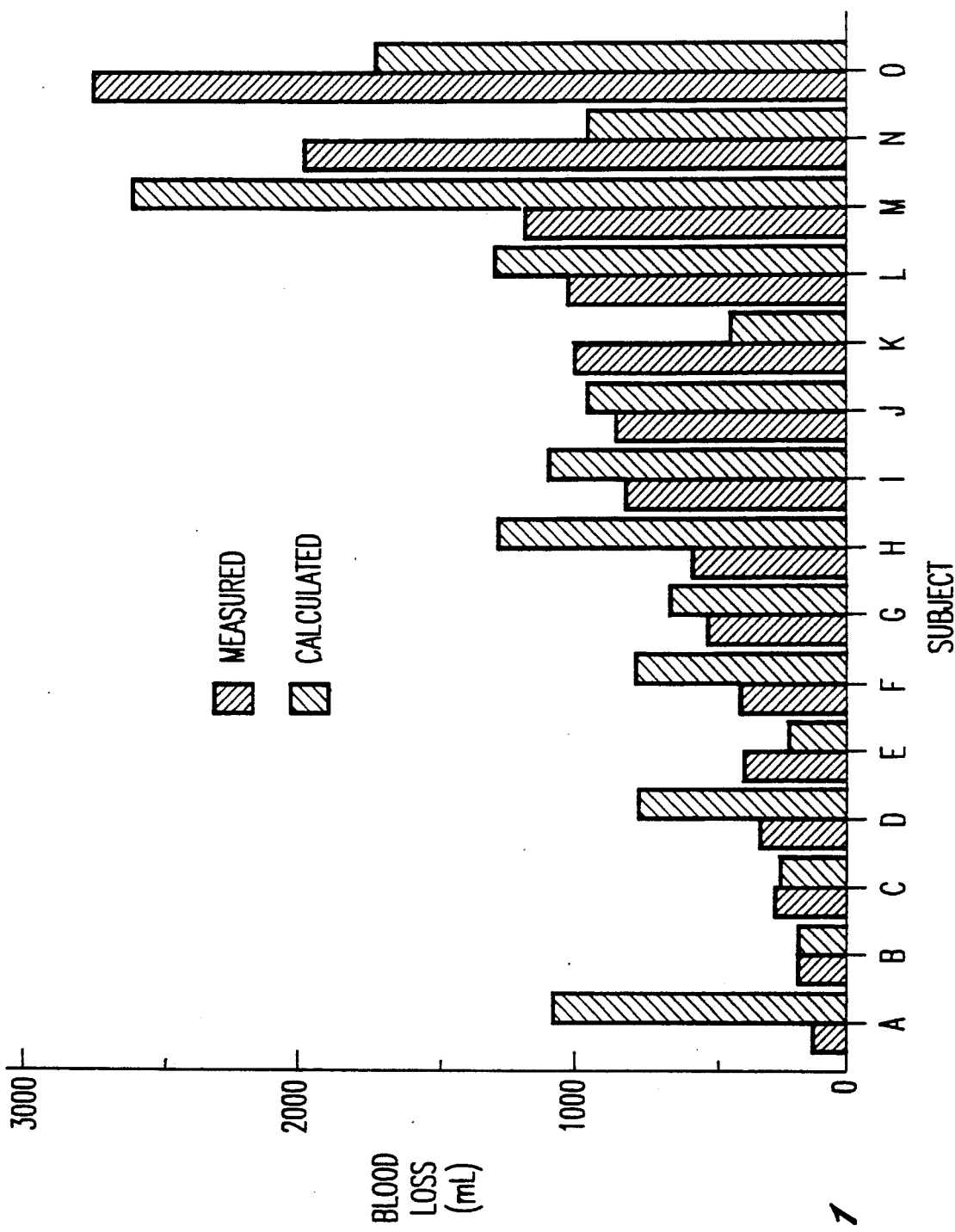
FIG. 1

Comparison of actual blood loss values and calculated blood loss values based on hematocrit values obtained from the patient.

FIG. 2

Comparison of actual blood loss values and estimates of blood loss by operating surgeon and anesthetist.

DETAILED DESCRIPTION OF THE INVENTION:

The inventive method is based on the use of a starting eluent of relatively low ionic strength, particularly characterized by a buffer and a volume control ion. Thus, blood is released from blood-bearing materials, and liquids, into the eluent, to produce the blood-containing eluate. In order to measure Hb content, red blood cells must be subjected to hemolysis. Direct osmotic hemolysis of most red blood cells (RBC) will occur at concentrations of osmotically active substances below about 0.05 moles/L. Assuming a blood/eluent ratio by volume, of 1:6, the blood may contribute about 0.025 moles of osmotically active substances per liter of eluate. Accordingly, the buffer concentration, and volume indicator ion concentration, should not exceed about 0.025 moles/L, to ensure hypotonicity. A preferred range, purely for a margin of error, provides a buffer strength of about 0.01–0.02 moles/L.

The pH of the buffer is of some importance. Proteins, including Hb are sensitive to pH. Additionally, as Hb content is measured by photometric observation of cyanmethemoglobin, pH becomes important, as the color intensity is pH dependent. Optimum pH for cyanmethemoglobin formation is about 6.5. A preferred pH range for the buffer is therefore about 6.2–6.6. In the assay, a pH of up to 6.8 can be tolerated. As the admixture of blood to the eluent will tend to increase the pH, the pH of the buffer may be varied, to a broader range of 5.8–6.8.

Traditional phosphate buffers have been used in biological work, and have pH values near or slightly below 7, and can be used in the inventive method. Other, more sophisticated buffer materials can be used, as long as the maximum buffer capacity is near a pH of about 6.5, thus the pK should be about 6.5. Such alternative buffers include BIS-TRIS, ADA, ACES, PIPES and MOPSO, currently available from Sigma. Any biologically compatible buffer of about 6.5 can be used.

As noted above, prior to the operation, a volume control substance, measurable by ion-selective electrode, is added to the eluent. This is because it is impossible to determine, in advance, changes in volume to be expected. It is to be noted that although the addition of blood will change the volume, a large variety of other materials, including patient fluids other than blood, and liquids employed in the operation, as well as solids added thereto, may change the overall perceived volume. The ion-selective electrode provides a means for direct monitoring of the ionic concentration of the control substance, and thus, the actual volume obtained. In addition to being sensitive to ion-selective electrodes, rather than electrodes measuring concentration based on a reaction taking place, the volume control substance cannot be drawn from species that could be contributed by the admixed blood or materials employed in the operation and likely to find their way to the eluent bath. Thus, ionic species such as $Na^+$, $K^+$, $Ca^{++}$, $Mg^{++}$, $Fe^{++}$, $Fe^{+++}$, $Zn^{++}$, $Cu^{++}$, $Cr^{+++}$, $I^-$, $IO_3^-$, $H_2PO_4^-$, $HPO_4$, $Cl^-$, $HCO_3^-$, are not suitable for use as volume control substances. Gases, being too unstable in concentration, must similarly be avoided. Although $CN^-$ would be unlikely to be contributed by the blood, or materials used during the operation, it participates in the Hb assay for blood loss determination, and similarly cannot be used. The remaining materials for which electrodes currently exist include $Br^-$, $Cd^{++}$, $NO_3^-$, $SCN^-$ and $Li^+$. $Cd^{++}$ and $NO_3^-$ are likely to be interfered with by blood constituents which vary in concentration as the procedure progresses, or are directly interfered with or bound by proteins likely to be obtained. Thus, $Li^+$, $SCN^-$ and $Br^-$ are preferred ionic volume control substances. As additional ion-selective electrodes become available, ions sensitive to those electrodes, meeting the above conditions, can similarly be used.

As noted above, osmotic hemolysis of the RBC is an essential step in the reaction. By maintaining a low ionic strength of eluent, effective osmotic swelling and bursting of the RBC can be obtained. However, to ensure substantially complete hemolysis, a hemolysis accelerator may be added to the eluent. Saponin is a commonly available agent, suitable for use in connection with the claimed invention. Other known hemolyzing agents may be used.

In the practice of the invention, the eluent is prepared, and placed in an enclosure which can be subjected to ultrasonic vibration. As solid materials bearing blood, e.g., pads, drapes, sponges and the like, accumulate significant amounts of the blood, they are added to the eluent. Simultaneously, and continuously, blood-containing liquids, such as blood, irrigation fluid, etc., are added directly to the eluent. Mixing can be preferentially achieved by injection of air pulses. The pulses may be directed simply from the bottom of the enclosure or in a variety of directions, to improve mixing, to avoid packing of fabric materials and the like. Together, all blood-bearing materials, liquid and solid, are referred to herein as blood-bearing materials.

The eluent is subjected to ultrasonic agitation or vibration, on a continuous basis. Mechanical reciprocating action is an alternative method. What is necessary is a means to continually bathe and wash the fabrics, and other solid materials added to the eluent to release all blood therefrom. While comminution of all solid material is an alternative to ensure blood release, this alternative creates unreasonably high turbidity, rendering photometric assays difficult.

If done on a non-automated basis, at appropriate moments, samples from the assay are drawn. If extreme turbidity is presented, centrifuging of the samples may be practiced. The volume control substance concentration is directly assayed, by use of the ion selective electrode. If lithium is the selected volume control substance, a lithium-selective electrode is used on samples of the eluate to be assayed for Hb content. If an automated system is used, the electrode is held in a flow-through cuvette, fed from the eluate preferably via a probe and a peristaltic pump, although other sampling methods are known and are useful. The cuvette also holds a reference electrode, giving direct and constant concentration information.

To make a Hb determination, aliquots of the sample are treated with additional buffer and potassium ferricyanide. This converts all Hb present in the sample to methemoglobin. Photometry at 632 nm gives the absorbances of all extraneous matter and methemoglobin. Cyanide added to the samples gives the combined absorbance of all extraneous matter reading at that value, with all Hb converted to cyanmethemoglobin and thus not absorbing at 632 mn. Alternatively, photometry at 540 mn will give the same differential as an increase, due to absorbance by cyanmethemoglobin. The difference between the two reading is proportional to the concentration of Hb. Thus, although the extraneous matter is also read at the absorbance values indicated, the contribution is cancelled out.

Thus, the actual volume of eluate, hemoglobin and actual blood loss, is determined according tot equations I-III below.

CALCULATIONS:

Current Volume (in L):

$$\text{Initial Volume (in L)} \times \frac{\text{Initial Li}^+\text{-conc.}}{\text{Current Li}^+\text{-conc.}}$$

Current Hb-conc (in g):
Current Hb-conc. (in g/L) × Current Volume (in L)

Current Blood Loss (in mL):

$$\text{Current Hb-amount (in g)} \times \frac{100}{\text{Pat.s' Hb-conc (in g/dL)}}$$

As each of the necessary values can be obtained on an immediate and continuous basis, real time values, or at the most real time plus no more than about five minutes, can be obtained, and communicated to the operating room to provide a continual update on the patient's blood loss. It is to be noted that the patient's hemoglobin concentration should be obtained immediately prior to the operation, as this concentration will vary over time. It should also be noted that if the patient is on, e.g., lithium therapy, an alternate volume control agent should be used, as the patient's own fluids will affect the volume determination, and thus the overall blood lost.

Advantageously, the Hb photometry is conducted by using a sample probe for the eluate, connected to a two-channel, continuous-flow fluid processing system. One channel carries sample, buffer, ferricyanide, water and air. The remaining channel carries sample, buffer, ferricyanide, cyanide and air. Both channels pump the components in identical proportion. The channels are read at either 540 nm or 632 nm. The difference in absorbance between the first and second channel is proportional to the concentration of Hb. In such a system, the lithium flow-through cuvette described above is used for volume determination.

EXAMPLES

The above method has been tested in both in vitro and in vivo experiments. In vitro experiments included adding measured amounts of blood, with known Hb values, onto sponges, pads and the like. These were allowed to soak and partially dry out. The pads were subjected to a phosphate buffer eluent, as described, and subjected to the analysis required. The results yielded recoveries of 95-102% of the measured amount added.

In an in vivo experiment, a dog was anesthetized, a cannula inserted in a femoral vein. 500 mL of blood was gradually removed from the dog, poured onto fabrics, tabletops and the like, and allowed to clot. After extraction according to the above-described process the blood loss determined was 98% of the actual 500 mL obtained.

The same method was applied on a selective basis in certain operating rooms. Blood losses, as measured according to the method of the invention were compared to blood loss calculated from hemoglobin/hematocrit values obtained immediately before, and approximately 24 hours after the procedure. The results are reflected in FIG. 1. As can be seen by inspection of the figure, actual values, as opposed to calculated values, vary substantially in both directions.

Figure 2:
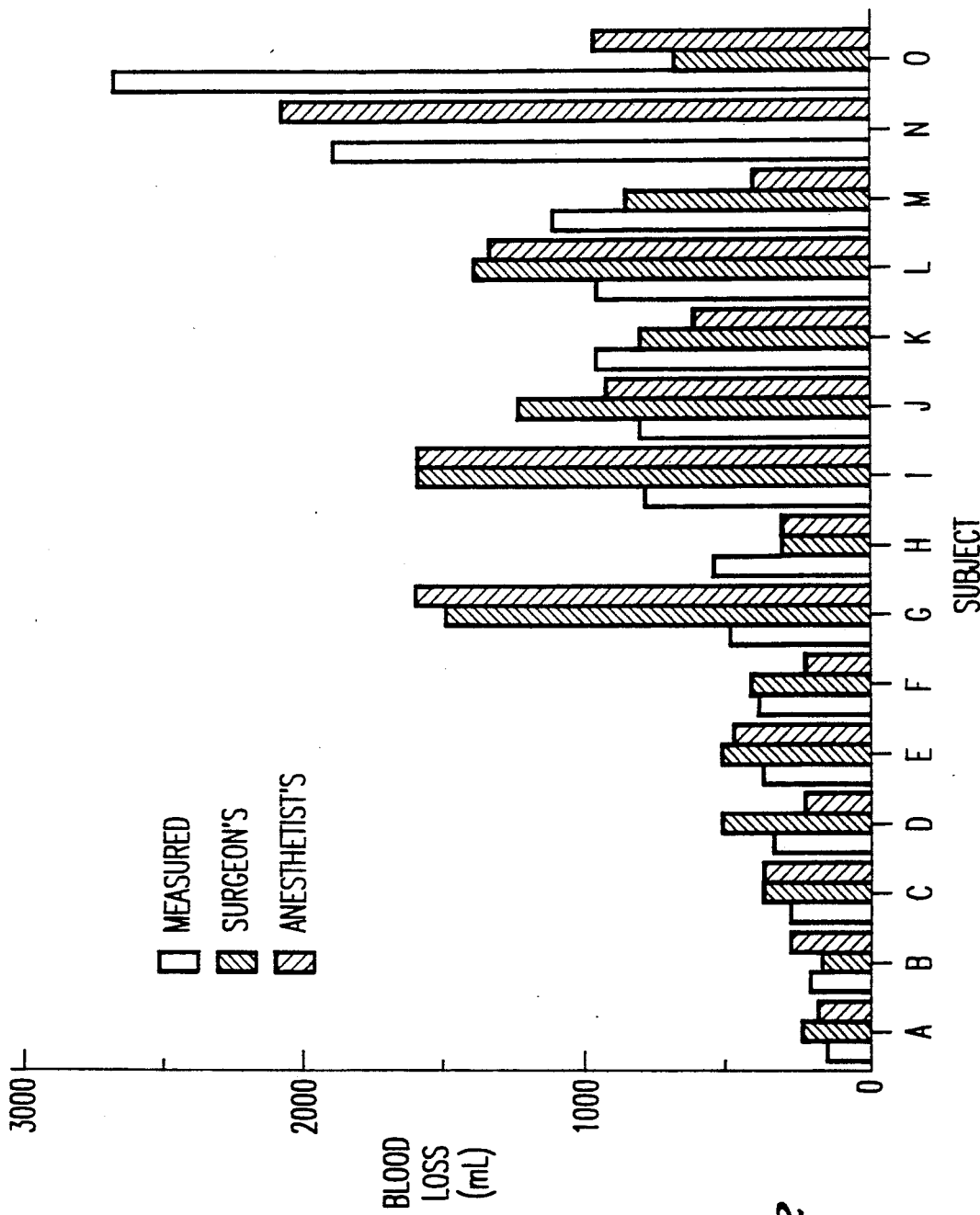

As noted above, one advantage of the system described is that it provides for real time monitoring. Currently, much real time work is based on the estimates made by the surgeon and anesthetist in the operating theater. The estimates were compared with the actual blood losses measured according to the above process. The results are illustrated in FIG. 2. Again, sharp differentials were observed.

The invention has been described above with reference both to specific example, and generic description. Alternatives will occur to those of ordinary skill in the art without the exercise of inventive faculty. In particular, substitutions of specific components, sampling methods, concentrations and related values, may be made, without departing from the invention, save as limited by the claims set forth below.

What is claimed is:

1. A method for monitoring a mammalian patient's blood loss during a surgical operation on said patient comprising the steps of:

determining the hemoglobin concentration i the blood of said patient immediately prior to said operation, collecting all blood-bearing materials generated during said operation, adding said materials to an eluent comprised of a buffer and a volume control substance selected from the group consisting of Li$^+$, SCN$^-$ and Br$^-$ in a known concentration, said buffer being hypnotic to red blood cells in said materials, such that said red blood cells undergo osmotic hemolysis, subjecting said eluent containing said materials to ultrasonic vibration in order to release blood from solid materials added to said eluent, thereby providing a blood-containing buffered solution, determining hemoglobin concentration in said blood-containing buffered solution after said ultrasonic vibration has released blood from said materials, determining the concentration of said volume control substance in said buffered solution and obtaining thereby the volume of said buffered solution after the foregoing steps have been performed, and calculating the actual amount of blood lost in said patient by multiplying he hemoglobin concentration in said blood-containing buffered solution by the volume of said buffered solution after said steps have been performed, and adjusting that value on the basis of hemoglobin concentration in the blood of said patient determined immediately prior to said operation.

2. The method of claim 1, wherein said volume control substance is lithium.

3. The method of claim 1, wherein said buffer has a pH in the range of 5.8–6.8.

4. The method of claim 1, wherein said eluent further comprises a hemolysis agent.

5. The method of claim 4, wherein said hemolysis agent is saponin.

6. The method of claim 1, wherein said hemoglobin concentration in said blood-containing buffered solution is determined photometrically.

7. The method of claim 6, wherein the photometric determination of said hemoglobin concentration comprises obtaining a sample of said blood-containing buffered solution, converting all hemoglobin therein to methemoglobin by reaction of the blood-containing buffered solution with potassium ferricyanide and obtaining the absorbance of said sample at 540 nm or 532 nm, converting said methemoglobin to cyanmethemoglobin by addition of cyanide to said sample, obtaining the absorbance for said cyanide-treated sample at said 540 nm or 632 nm, and calculating the difference between the two absorbance values obtained which is proportional to the hemoglobin concentration in said sample.

8. The method of claim 1, wherein said monitoring of blood loss is conducted repeatedly during said operation.

9. The method of claim 8, wherein said repeated monitoring is made and communicated to those operating on said patient within five minutes of the time the monitoring occurs.

10. The method of claim 1, wherein said blood loss monitoring is made continuously during said operation.

11. The method of claim 10, wherein said blood loss monitoring is communicated to those operating on said patient within five minutes of the time the monitoring occurs.

* * * * *

UNITED STATES PATENT AND TRADEMARK OFFICE
CERTIFICATE OF CORRECTION

PATENT NO. : 5,231,032
DATED : JULY 27, 1993
INVENTOR(S) : BERNARD LUDVIGSEN

It is certified that error appears in the above-indentified patent and that said Letters Patent is hereby corrected as shown below:

Column 2, line 6, "i" should read --in--;
    line 34, "o" should read --on--;
    line 44, "spectrohotometric" should read --spectrophotometric--;
    line 53, "623 nm" should read --632 nm--;
    line 60, delete "," after "concentration".

Column 3, line 48, "Traditional" should read --Traditionally--.

Column 4, line 43, after "achieved by", insert --mechanical action or--;
    line 59, delete "," after "ments".

Column 5, line 15, "reading" should read --readings--;
    line 20, "tot" should read --to the--;
    line 23, after "Initial $Li^+$-conc." in the right hand margin, insert --(I)--;
    line 28, after "Current Volume (in L)" in the right hand margin, insert (II)--;
    line 31, after "100" in the right hand margin, insert --(III)--;
    line 35, "the most real time" should read --the most values in real time--;
    line 36, delete "," after "obtained";
    line 44, "the overall blood" should read --the overall values for blood--.

UNITED STATES PATENT AND TRADEMARK OFFICE
CERTIFICATE OF CORRECTION

PATENT NO. : 5,231,032
DATED : JULY 27, 1993
INVENTOR(S) : BERNARD LUDVIGSEN

It is certified that error appears in the above-indentified patent and that said Letters Patent is hereby corrected as shown below:

Column 6, line 36, "i" should read --in--;
         line 45, "hypnotic" should read --hypotonic--;
         line 60, "he" should read --the--.

Column 7, line 16, "532" should read --632--.

Signed and Sealed this

Nineteenth Day of April, 1994

Attest:

BRUCE LEHMAN

Attesting Officer     Commissioner of Patents and Trademarks